United States Patent [19]

Lagrange et al.

[11] Patent Number: 5,516,942
[45] Date of Patent: May 14, 1996

[54] HYDROXYETHYLATED 2-NITRO-P-PHENYLENEDIAMINES AND USE THEREOF FOR DYEING KERATIN FIBERS

[75] Inventors: Alain Lagrange, Coupvray; Alex Junino, Livry-Gargan; Alain Genet, Aulnay-sous-Bois; Jean Cotteret, Verneuil-sur-Seine, all of France

[73] Assignee: L'Oreal, Paris, France

[21] Appl. No.: 351,242

[22] PCT Filed: Jun. 15, 1993

[86] PCT No.: PCT/FR93/00571

§ 371 Date: Dec. 7, 1994

§ 102(e) Date: Dec. 7, 1994

[87] PCT Pub. No.: WO94/00415

PCT Pub. Date: Jan. 6, 1994

[30] Foreign Application Priority Data

Jun. 19, 1992 [FR] France ..................... 92 07516

[51] Int. Cl.$^6$ .................... A61K 7/13; C07C 215/16
[52] U.S. Cl. .................. 564/441; 8/415
[58] Field of Search ................. 564/441; 8/415

[56] References Cited

U.S. PATENT DOCUMENTS

| 3,555,584 | 1/1971 | Kalopissi et al. ............... 8/415 |
| 4,007,228 | 2/1977 | Kalopissi et al. ............... 564/441 X |
| 4,921,504 | 5/1990 | Clausen et al. ................ 8/415 |

FOREIGN PATENT DOCUMENTS

| 184061 | 6/1986 | European Pat. Off. . |
| 1454314 | 9/1966 | France . |

Primary Examiner—Richard L. Raymond
Attorney, Agent, or Firm—Jacobson, Price, Holman & Stern

[57] ABSTRACT

A N1,N4-dihydroxyethylated 2-nitro-p-phenylenediamine of formula (I), wherein R is C3-4 aklyl, and cosmetically acceptable salts thereof, for use in direct dyeing to give blue through purple shades which are wash-fast, light-fast, weatherproof and sweat resistant, and optionally combined with yellow and optionally read or orange-coloured dyes to give natural hues.

21 Claims, No Drawings

HYDROXYETHYLATED 2-NITRO-P-PHENYLENEDIAMINES AND USE THEREOF FOR DYEING KERATIN FIBERS

This application is a 371 of application PCT/FR93/00571, filed Jun. 15, 1993.

The present invention relates to novel nitrobenzene dyes of 2-nitro-p-phenylenediamine type, which are intended for dyeing keratin fibers and in particular human hair.

In the field of hair dyeing, the use of direct dyes is very widespread since they have certain advantages with respect to oxidation dye precursors and, in particular, a reduction in the potential risks of allergy and the absence of sensitization of the hair caused by the oxidative process.

Nitrobenzene derivatives feature among the most commonly used direct dyes, which derivatives, on the one hand, have a high affinity for hair, and which, on the other hand, due to the variety of possible substitutes, make it possible to cover a wide spectrum of shades ranging from yellow to blue and including red.

Among the blue or blue-purple nitro dyes used, there may be mentioned 1-β-hydroxyethylamino- 4-N,N-bis(β-hydroxyethyl)amino-2-nitrobenzene described in French Patent 1 101 904, 1-β-hydroxyethylamino- 4-(N-methyl-N-β-hydroxyethyl)amino-2-nitrobenzene described in Canadian Patent 900 490, and 1-β-hydroxy-ethylamino- 4-(N-ethyl-N-β-hydroxyethyl)amino-2-nitrobenzene described in Patent EP-0 184 061.

However, the formulation of these nitro dyes poses problems on account of their resistance to washing, which is not satisfactory.

The Applicant has thus sought other nitrobenzene dyes which have shades graduating from blue to purple and which have good solubility in water, in water/alcohol mixtures and more generally in the usual dye supports, and which lead, on hair, to dyes which are wash-fast and light-fast, weather-proof and sweat-resistant.

As a result of this research, the Applicant has discovered novel 2-nitro-p-phenylenediamines having the formula:

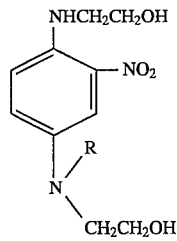

in which R represents a linear or branched alkyl radical containing 3 or 4 carbon atoms.

Among the alkyl radicals R, there may be mentioned n-propyl, isopropyl, n-butyl, isobutyl and tert-butyl radicals, the preferred radicals being n-propyl and isobutyl.

The compounds of formula (I) may be used in free base form or in the form of a base salified with acids such as hydrochloric acid, hydrobromic acid, sulfuric acid, etc. They may thus be found in the form of a hydrochloride, a hydrobromide, a sulfate, etc.

The present invention thus relates to the novel compounds of formula (I) and to the cosmetically acceptable salts thereof.

The compounds of formula (I) are prepared by a standard alkylation process which consists in reacting, in an aqueous medium and at a temperature between room temperature and the reflux temperature of the medium, 1,4-di(β-hydroxyethylamino)-2-nitrobenzene with a haloalkane such as a bromo-, iodo- or chloroalkane, in the presence of calcium carbonate, optionally followed by purification of the compound obtained.

The invention also relates to a dye composition for the direct dyeing of keratin fibers and in particular human hair, which composition contains, in an aqueous, alcoholic or aqueous-alcoholic vehicle, at least one compound of formula (I) or one of the cosmetically acceptable salts thereof.

The Applicant has observed that the combination of a blue to purple nitrobenzene dye of formula (I), in compositions for direct dyeing, with yellow or green-yellow dyes and optionally with orange or red dyes, leads to the production of natural shades which are wash-fast, light-fast, weather-proof and sweat-resistant.

In a preferred embodiment, the dye composition according to the invention thus contains a compound of formula (I), or one of the cosmetically acceptable salts thereof, in combination with one or more yellow or green-yellow nitrobenzene dyes, which give, on gray hair containing 90% white hairs, a shade or "hue" of between 2.5 Y and 2.5 GY on the Munsell circle (see Official Digest publication, April 1975, page 375, figure 2).

In a more particularly preferred embodiment of the present invention, the compound of formula (I) is combined with yellow or green-yellow dyes chosen from the following compounds:

Yellow or green-yellow dyes
1-β-hydroxyethyloxy-3-methylamino-4-nitrobenzene,
1-(methylamino)-2-nitro-5-(β,γ-dihydroxypropyl)oxybenzene,
1-(β-hydroxyethylamino)-2-methoxy-4-nitrobenzene,
1-(β-aminoethylamino)-2-nitro-5-methoxybenzene,
1,3-di(β-hydroxyethylamino)-4-nitro-6-chlorobenzene,
1-amino-2-nitro-6-methylbenzene,
1-(β-hydroxyethylamino)-2-hydroxy-4-nitrobenzene,
N-(β-hydroxyethyl)-2-nitro-4-trifluoromethylaniline,
4-β-hydroxyethylamino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-β-ureidoethylamino-4-nitrobenzene,
O,N-bis(β-hydroxyethyl)-2-amino-5-nitrophenol,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl) amino-2-nitrobenzene,
4-(β-hydroxyethylamino)-3-nitrobenzamide.

The compound of formula (I) may also be combined with the following red or orange dyes:

Red dyes
1-hydroxy-3-nitro-4-(γ-hydroxypropylamino)benzene,
N-(β-hydroxyethyl)amino-3-nitro-4-aminobenzene,
1-amino-3-methyl-4-(β-hydroxyethyl)amino-6-nitrobenzene,
1-hydroxy-3-nitro-4-N-β-hydroxyethylaminobenzene,
1,4 -diamino-2 -nitrobenzene,
1-amino-2-nitro-4-methylaminobenzene,
N-(β-hydroxyethyl)-2-nitro-para-phenylenediamine,
1-amino-2-nitro-4-(β-hydroxyethylamino)-5-chlorobenzene,
2-nitro-4-aminodiphenylamine,
1-amino-3-nitro-6-hydroxybenzene.

Orange dyes 1-(β-aminoethyl)amino-2-nitro-4-(β-hydroxyethyl)oxybenzene,
1-(β,γ-dihydroxypropyl)oxy-3-nitro-4-(β-hydroxyethyl)aminobenzene,
1-hydroxy-3-nitro-4-aminobenzene,
1-hydroxy-2-amino-4,6-dinitrobenzene,
1-methoxy-3-nitro-4-(β-hydroxyethylamino)benzene,
2-nitro-4'-hydroxydiphenylamine,
1-amino-2-nitro-4-hydroxy-5-methylbenzene.

The dye composition according to the invention contains 0.01 to 10% by weight, and preferably 0.1 to 5% by weight, expressed as free base, of nitrobenzene dye of formula (I).

The total concentration of yellow or green-yellow dyes may be between 0.05 and 3% by weight, based on the total weight of the dye composition.

It is, of course, possible to add other direct dyes to the dye composition according to the invention, such as azo dyes, anthraquinone dyes, dyes derived from triarylmethane or basic dyes, among which there may more particularly be mentioned the dyes known under the names "Basic Brown 16", "Basic Yellow 57", "Basic Red 76" and "Basic Blue 99∞ in the COLOR INDEX, 3rd edition.

The proportion of the addition dyes, which may be red or orange nitrobenzene dyes or other direct dyes, may range between 0.05 and 10% of the weight of the composition.

The dye composition according to the invention may comprise, as suitable vehicle, water and/or organic solvents which are acceptable from a cosmetic viewpoint, and more particularly alcohols such as ethyl alcohol, isopropyl alcohol, benzyl alcohol and phenethyl alcohol, or glycols or glycol ethers such as, for example, ethylene glycol and the monomethyl, monoethyl and monobutyl ethers thereof, propylene glycol, butylene glycol and dipropylene glycol, as well as diethylene glycol alkyl ethers such as, for example, diethylene glycol monoethyl ether or monobutyl ether, in concentrations of between 0.5 and 20%, and preferably of between 2 and 10%, relative to the total weight of the composition.

Fatty amides such as the mono- and diethanoiamides of acids derived from coconut, from lauric acid or from oleic acid, may also be added to the composition according to the invention, in concentrations of between 0.05 and 10% by weight.

Anionic, cationic, nonionic or amphoteric surface-active agents, or mixtures thereof, may also be added to the composition according to the invention. The surfactants are preferably present in the composition according to the invention in a proportion of between 0.1 and 50% by weight, and advantageously of between 1 and 20% by weight, relative to the total weight of the composition.

Among the surface-active agents, there may more particularly be mentioned anionic surface-active agents which are used alone or as a mixture, in particular such as alkali metal salts, magnesium salts, ammonium salts, amine salts or alkanolamine salts of the following compounds:

alkyl sulfates, alkyl ether sulfates, alkyl amide sulfates which may or may not be ethoxylated, alkyl sulfonates, alkyl amide sulfonates, α-olefin sulfonates;

alkyl sulfoacetates, alkyl phosphates;

fatty acids such as lauric acid, myristic acid, oleic acid, ricinoleic acid, palmitic acid, stearic acid, acids of coconut oil or of hydrogenated coconut oil, carboxylic acids of polyglycol ethers, the alkyl radicals of these compounds having a side chain of 12 to 18 carbon atoms.

As cationic surface-active agents, there may more particularly be mentioned fatty amine salts, quaternary ammonium salts such as the alkyldimethylbenzylammonium, alkyltrimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long-chain groups which preferably have between 12 and 18 carbon atoms.

Amine oxides may also be mentioned among these compounds of cationic nature.

Among the amphoteric surface-active agents which may be used, there may in particular be mentioned alkylamino (mono- and di)propionates, betaïnes such as alkyl beta ïnes, N-alkyl sulfobetaïnes, N-alkylamino betaïnes, the alkyl radical having between 8 and 22 carbon atoms, and cycloimidiniums such as alkylimidazolines.

Among the nonionic surfactants which may optionally be used in the compositions in accordance with the invention, there may be mentioned alcohols, α-diols, alkylphenols and amides, which are polyglycerated, these compounds containing a $C_8$–$C_{18}$ fatty chain;

alcohols, alkylphenols and fatty acids, which are polyethoxylated, these compounds containing a $C_8$ to $C_{18}$ fatty chain;

condensates of ethylene oxide and of propylene oxide on fatty alcohols; polyethoxylated fatty amides, containing at least 5 mol of ethylene oxide;

polyethoxylated fatty amines.

The thickening products which may be added to the composition according to the invention may advantageously be taken from the group formed by sodium alginate, gum arabic, guar gum, xanthan gum, carob gum, cellulose derivatives such as methylcellulose, hydroxyethylcellulose, hydroxypropylmethylcellulose, the sodium salt of carboxymethylcellulose and acrylic acid polymers.

Inorganic thickening agents such as bentonite may also be used. These thickening agents are used alone or as a mixture, and are preferably present in a proportion of between 0.2 and 5% by weight relative to the total weight of the composition, and advantageously of between 0.5 and 3% by weight.

The dye composition according to the invention may be formulated at acidic, neutral or alkaline pH, the pH possibly ranging from 4 to 10.5, and preferably from 5 to 10. Among the basifying agents which may be used, there may be mentioned alkanolamines, alkali metal hydroxides or carbonates and ammonium hydroxide or ammonium carbonate. Among the acidifying agents which may be used, there may be mentioned lactic acid, acetic acid, tartaric acid, phosphoric acid, hydrochloric acid and citric acid.

The dye composition according to the invention may additionally contain various common adjuvants, such as antioxidants, fragrances, sequestering agents, film-forming products, hair-treatment agents, dispersing agents, hair-conditioning agents, preserving agents, opacifying agents and any other adjuvant which is usually used in cosmetics.

The dye composition according to the invention may be provided in the various forms commonly used for dyeing hair, such as liquids which are thickened or gelled, creams, aerosol foams or any other forms which are suitable for dyeing keratin fibers.

The present invention also relates to a process for dyeing keratin fibers, and in particular human hair, which consists in allowing the dye composition defined above to act on the dry or wet keratin fibers. The composition according to the invention may be used as a non-rinsed lotion, that is to say that the composition according to the invention is applied to the keratin fibers and is then dried without intermediate rinsing. In other modes of application, the dye composition according to the invention is applied to the keratin fibers for an exposure time ranging between 3 and 60 minutes, preferably between 5 and 45 minutes, and the fibers are rinsed, optionally washed and rinsed again, and then dried.

In order to gain a better understanding of the subject of the invention, several modes of implementation thereof will now be described, purely as guides and with no limitation being implied.

PREPARATION EXAMPLES

EXAMPLE 1

Preparation of 1-(β-hydroxyethyl)amino-4-(N-β-hydroxyethyl-N-n-propyl)-amino- 2-nitrobenzene hydrochloride, named according to the IUPAC nomenclature 2-{4-[(2-hydroxyethyl)propylamino]-2-nitrophenylamino}ethanol.

A suspension of 48.2 g (0.2 mmol) of 1,4-di(β-hydroxyethylamino)-2-nitrobenzene and 30 g of calcium carbonate in 80 ml of water is heated in a hot water bath (85° C.). 54.7 ml (0.6 mol) of 1-bromopropane are added dropwise over 1 hour and the heating is continued for 7 hours, the reaction being monitored by thin layer chromatography (silica gel: eluent: ethyl acetate).

The mixture is filtered while hot and the filtrate is cooled; the oil which precipitates is extracted with ethyl acetate.

The ethyl acetate phase is dried over sodium sulfate, filtered and evaporated to dryness under reduced pressure.

The oil obtained is purified by passage through a medium pressure column (silica gel; gradient of ethyl acetate and heptane).

After evaporation of the solvent to dryness, the free base is dissolved in 300 ml of absolute ethanol and 20 ml of approximately 7N hydrochloric acid solution in absolute ethanol are added.

The hydrochloride of the expected compound precipitates as yellow crystals, which are drained, washed with ethyl ether and dried over potassium hydroxide under vacuum.

36.0 g of hydrochloride are obtained, which product melts with decomposition at 168°–170° C. and the elemental analysis of which, calculated for $C_{13}H_{22}N_3O_4Cl$, is:

|  | C % | H % | N % | O % | Cl % |
| --- | --- | --- | --- | --- | --- |
| Calculated: | 48.83 | 6.93 | 13.14 | 20.01 | 11.09 |
| Found: | 49.08 | 6.95 | 12.99 | 20.10 | 10.98 |

EXAMPLE 2

Preparation of 1-(β-hydroxyethyl)amino-4-(N-β-hydroxyethyl-N-n-butyl)amino- 2-nitrobenzenehydrochloride, named according to the IUPAC nomenclature 2-{4-[butyl-(2-hydroxyethyl)amino]-2-nitrophenylamino}ethanol.

This compound is prepared and purified according to the procedure described for the above example.

Starting with 48.2 g (0.2 mol) of 1,4-di(β-hydroxyethylamino)-2-nitrobenzene and 1-iodobutane, yellow crystals of hydrochloride (35.0 g) are obtained, which product melts with decomposition at 160°–162° C. and the elemental analysis of which, calculated for $C_{14}H_{24}N_3O_4Cl$, is:

|  | C % | H% | N % | O % | Cl % |
| --- | --- | --- | --- | --- | --- |
| Calculated: | 50.37 | 7.25 | 12.59 | 19.17 | 10.62 |
| Found: | 50.45 | 7.34 | 12.45 | 19.06 | 10.56 |

EXAMPLE 3

Preparation of 1-(β-hydroxyethyl)amino-4-(N-β-hydroxyethyl-N-isobutyl)amino- 2-nitrobenzene hydrochloride, named according to the IUPAC nomenclature 2-{4-[(2-hydroxyethyl)isobutylamino]-2-nitrophenylamino}ethanol.

This compound is prepared and purified according to the procedure described for Example 1.

Starting with 48.2 g (0.2 mol) of 1,4-di(β-hydroxyethylamino)-2-nitrobenzene and 1-iodo- 2-methylpropane, yellow crystals of hydrochloride (20.4 g) are obtained, which product melts with decomposition at 152°–154° C. and the elemental analysis of which, calculated for $C_{14}H_{24}N_3O_4Cl$, is:

|  | C % | H % | N % | O % | Cl % |
| --- | --- | --- | --- | --- | --- |
| Calculated: | 50.37 | 7.25 | 12.59 | 19.17 | 10.62 |
| Found: | 50.60 | 7.19 | 12.48 | 19.35 | 10.68 |

EXAMPLES OF APPLICATION

EXAMPLE A

The following dye composition is prepared:

| 1-(β-Hydroxyethyl)amino-4-(N-β-hydroxyethyl-N-n-propyl)amino-2-nitrobenzene hydrochloride | 0.96 g |
| --- | --- |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol qs pH 9 | |
| Water qs | 100 g |

This composition is applied to natural gray hair containing 90% white hairs, and is left to stand for 30 minutes at room temperature. After rinsing, the hair is dyed a bluish ash color.

EXAMPLE B

The following dye composition is prepared:

| 1-(β-Hydroxyethyl)amino-4-(N-β-hydroxyethyl-N-n-butyl)amino-2-nitrobenzene hydrochloride | 1 g |
| --- | --- |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol qs pH 9 | |
| Water qs | 100 g |

This composition is applied to permanent-waved gray hair for 30 minutes at room temperature. After rinsing, the hair is dyed a dark purple-ash color.

EXAMPLE C

The following dye composition is prepared:

| | |
|---|---|
| 1-(β-Hydroxyethyl)amino-4-(N-β-hydroxy-ethyl-N-isobutyl)amino-2-nitrobenzene hydrochloride | 1 g |
| Propylene glycol monomethyl ether | 10 g |
| Coconut fatty acid diethanolamides | 2 g |
| Oxyethylenated nonylphenol containing 9 mol of ethylene oxide | 8 g |
| 2-Amino-2-methyl-1-propanol qs pH 9 | |
| Water qs | 100 g |

This composition is applied to permanent-waved gray hair for 30 minutes at room temperature. After rinsing, the hair is dyed a dark purple-ash color.

EXAMPLE D

The following dye composition is prepared:

| | |
|---|---|
| 1-(β-Hydroxyethyl)amino-4-(N-β-hydroxy-ethyl-N-n-propyl)amino-2-nitrobenzene hydrochloride | 0.3 g |
| 1-β-Hydroxyethyloxy-3-methylamino-4-nitrobenzene | 0.08 g |
| Oxyethyleneated nonylphenol containing 9 mol of ethylene oxide | 8 g |
| Coconut fatty acid diethanolamides | 2 g |
| Ethyl glycol [sic] | 10 g |
| Triethanolamine qs PH 9 | |
| Water qs | 100 g |

This composition is applied to natural gray hair containing 90% white hairs, for 20 minutes at room temperature. After rinsing, the hair is dyed a matt golden light blonde color.

We claim:

1. $N^1,N^4$-Dihydroxyethylated 2-nitro-p-phenylenediamine having the formula:

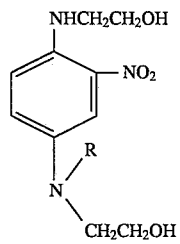

in which R represents a linear or branched alkyl radical containing 3 or 4 carbon atoms, and the cosmetically acceptable salts of this compound.

2. Compound according to claim 1, wherein the alkyl radical R is n-propyl, isopropyl, n-butyl, isobutyl or tert-butyl.

3. Compound according to claim 1, wherein it is 1-(β-hydroxyethyl)amino- 4-(N-β-hydroxyethyl-N-n-propyl)amino-2-nitrobenzene, 1-(β-hydroxyethyl)amino- 4-(N-β-hydroxyethyl-N-n-butyl)amino- 2-nitrobenzene and 1-(β-hydroxyethyl)amino- 4-(N-β-hydroxyethyl-N-isobutyl)amino-2-nitrobenzene or the cosmetically acceptable salts thereof.

4. Dye composition for the direct dyeing of keratin fibers, wherein in an aqueous, alcoholic or aqueous-alcoholic vehicle, at least one compound of formula (I) according to claim 1, or one of the cosmetically acceptable salts thereof.

5. Dye composition according to claim 4, wherein it contains a compound of formula (I) 1-(β-hydroxyethyl)amino-4-(N-β-hydroxyethyl-N-n-propyl)amino- 2-nitrobenzene, 1-(β-hydroxyethyl)amino- 4-(N-β-hydroxyethyl-N-n-butyl)amino-2-nitrobenzene or 1-(β-hydroxyethyl)amino-4-(N-β-hydroxyethyl-N-isobutyl)amino- 2-nitrobenzene.

6. Dye composition according to claim 4, wherein it contains at least one compound of formula (I), or one of the cosmetically acceptable salts thereof, in combination with at least one yellow or green-yellow nitrobenzene dye giving a Munsell shade of between 2.5 Y and 2.5 GY on gray hair containing 90% white hairs.

7. Dye composition according to claim 6, wherein the yellow or green-yellow nitrobenzene dye is chosen from the following compounds: 1-β-hydroxyethyloxy- 3-methylamino-4-nitrobenzene, 1-(methylamino)-2-nitro- 5-(β,γ-dihydroxypropyl)oxybenzene, 1-(β-hydroxy-ethylamino)-2-methoxy-4-nitrobenzene, 1-(β-aminoethylamino)- 2-nitro-5-methoxybenzene, 1,3-di(β-hydroxyethylamino)- 4-nitro-6-chlorobenzene, 1-amino-2-nitro-6-methylbenzene, 1(β-hydroxyethylamino)-2-hydroxy-4-nitrobenzene, N-(β-hydroxyethyl)-2-nitro-4-trifluoromethylaniline, 4-β-hydroxyethylamino-3-nitrobenzenesulfonic acid, 4-ethylamino-3-nitrobenzoic acid, 4-(β-hydroxyethyl)amino-3-nitrochlorobenzene, 4-(β-hydroxyethyl)amino- 3-nitromethylbenzene, 4-(β,γ-dihydroxypropyl)amino- 3-nitrotrifluoromethylbenzene, 1-β-ureidoethylamino- 4-nitrobenzene, O,N-bis(β-hydroxyethyl)-2-amino-5-nitrophenol, 1,3-diamino-4-nitrobenzene, 1-hydroxy-2-amino-5-nitrobenzene, 1-amino-2-[tris(hydroxymethyl)methyl]amino- 5-nitrobenzene, 1-(β-hydroxyethyl)amino-2-nitrobenzene or 4-(β-hydroxyethylamino)-3-nitrobenzamide.

8. Dye composition according to claim 4, wherein it additionally contains at least one red nitrobenzene dye chosen from the following compounds: 1-hydroxy-3-nitro-4-(β-hydroxypropylamino)benzene, N-(β-hydroxyethyl)amino-3-nitro-4-aminobenzene, 1-amino-3-methyl-4-(β-hydroxyethyl)amino-6-nitrobenzene, 1-hydroxy-3-nitro-4-N-β-hydroxyethylaminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethylamino)-5-chlorobenzene, 2-nitro-4-amino-diphenylamine or 1-amino- 3-nitro-6-hydroxybenzene.

9. Dye composition according to claim 4, wherein it additionally contains at least one orange nitrobenzene dye chosen from the following compounds: 1-(β-aminoethyl)amino-2-nitro-4-(β-hydroxyethyl)oxybenzene, 1-(β,γ-dihydroxypropyl-oxy-3-nitro- 4-(β-hydroxyethyl)aminobenzene [sic], 1-hydroxy-3-nitro- 4-aminobenzene, 1-hydroxy-2-amino-4,6-dinitrobenzene, 1-methoxy-3-nitro-4-(β-hydroxyethylamino)benzene, 2-nitro-4'-hydroxydiphenylamine or 1-amino-2-nitro- 4-hydroxy-5-methylbenzene.

10. Dye composition according to any one of claims 4 to 9, wherein it contains other direct dyes chosen from azo dyes, anthraquinone dyes, triarylmethane derivatives or basic dyes.

11. Dye composition according to claim 4, wherein it contains 0.01 to 10% by weight, expressed as free base, of a compound of formula (I).

12. The dye composition according to claim 11 characterized in that it contains 0.1 to 5% by weight expressed as free base of a compound of formula (I).

13. Dye composition according to claim 4, wherein it contains 0.05 to 3% by weight of yellow nitrobenzene dyes.

14. Dye composition according to claim 4, characterized in that it contains 0.05 to 10% by weight of other direct dyes.

15. Dye composition according to claim 4, wherein it contains organic solvents concentrations of between 0.5 and 20% by weight, relative to the total weight of the composition.

16. Dye composition according to claim 4, wherein it contains at least one adjuvant chosen from fatty amides in concentrations of between 0.05 and 10% by weight, anionic, cationic, nonionic or amphoteric surface-active agents, or mixtures thereof, in concentrations of between 0.1 and 50% by weight, thickening agents in concentrations of between 0.2 and 5% by weight, antioxidants, fragrances, sequestering agents, film-forming agents, hair-treatment agents, dispersing agents, hair-conditioning agents, preserving agents or opacifying agents.

17. Dye composition according to claim 4, herein it has a pH of between 4 and 1.05.

18. Process for dyeing keratin fibers, by direct dyeing, wherein that the dye composition according to claim 4 is applied to the dry or wet keratin fibers, and they are dried without intermediate rinsing.

19. The process for dyeing keratin fibers according to claim 18 wherein the keratin fiber is human hair.

20. Process for dyeing keratin fibers, by direct dyeing, wherein the dye composition according to claim 4 is applied to the dry or wet keratin fibers, and in that, after leaving the composition to act for 3 to 60 minutes, the keratin fibers are rinsed and then dried.

21. The process for dyeing keratin fibers according to claim 20 wherein the keratin fiber is human hair.

* * * * *